United States Patent [19]

Chew et al.

[11] Patent Number: 4,906,772

[45] Date of Patent: Mar. 6, 1990

[54] PROCESS FOR PRODUCTION OF POLYCARBOXYLIC AROMATIC ACIDS

[75] Inventors: Calvin T. Chew, Warrenville; Rosemary F. McMahon, Wheaton; Kristi A. Fjare; Wayne P. Schammel, both of Naperville, all of Ill.

[73] Assignee: Amoco Corporation, Chicago, Ill.

[21] Appl. No.: 279,411

[22] Filed: Dec. 2, 1988

[51] Int. Cl.$^4$ .................. C07C 51/265; C07C 51/235
[52] U.S. Cl. ...................................... 562/416; 560/77; 560/239; 562/414; 562/417; 562/538
[58] Field of Search ............... 562/414, 416, 417, 538; 560/77, 239

[56] References Cited

U.S. PATENT DOCUMENTS

| | | | |
|---|---|---|---|
| 4,172,209 | 10/1979 | Vora .................................. | 562/414 |
| 4,769,488 | 9/1988 | Nowicki et al. ..................... | 562/414 |
| 4,792,621 | 12/1988 | Abrams ............................... | 562/414 |
| 4,827,026 | 5/1989 | Brugge et al. ...................... | 562/416 |

*Primary Examiner*—Werren B. Lone
*Assistant Examiner*—Vera C. Clarke
*Attorney, Agent, or Firm*—Gunar J. Blumberg; William H. Magidson; Ralph C. Medhurst

[57] ABSTRACT

A process is disclosed for the co-production of aliphatic monocarboxylic acids and polycarboxylic aromatic acids in high selectivity, conversion and yield. The aliphatic monocarboxylic acid can serve as a component of the solvent for the process.

12 Claims, No Drawings

PROCESS FOR PRODUCTION OF POLYCARBOXYLIC AROMATIC ACIDS

FIELD OF THE INVENTION

This invention relates to an improved process for the preparation of polycarboxylic aromatic acids. More particularly, it relates to an improved process for the preparation of terephthalic acid from p-xylene and the preparation of trimellitic acid from pseudocumene wherein acetic acid necessary as a solvent for the liquid phase oxidation of the precursors is generated in situ by oxidation of ethanol as a co-oxidized starting material. Co-generation of acetic acid by oxidation of ethanol in production of polycarboxylic aromatic acids reduces the economic costs of producing polycarboxylic aromatic acids from polyalkyl aromatic compounds, uses available process equipment without major modification, and provides an alternate method of supplying necessary acetic acid to the oxidation processes for preparation of aromatic polycarboxylic acids. This invention also relates to a process for preparation of polycarboxylic aromatic acids in the presence of a $C_2$–$C_6$ monocarboxylic acid as solvent, wherein the monocarboxylic acid of 2 to 6 carbon atoms is co-produced by oxidation of a aliphatic alkanol of 2 to 6 carbon atoms.

BACKGROUND OF THE INVENTION

Acetic acid, one of the more important aliphatic intermediates, quantitatively ranks among the commodity chemicals produced in large tonnage quantities. However, availability of acetic acid for downstream applications can be limited at times since availability and price of feedstocks for the production of acetic acid are subject to constant change. For example, availability of hydrocarbon feedstocks such as ethylene, butane and butenes from petroleum and natural gas sources can vary widely depending upon supplies of crude oil upon the world market, capacity of petrochemical producers and demand for products which utilize these same hydrocarbons as feedstocks. An example is polyethylene from ethylene.

Acetic acid can be manufactured by one of several processes, i.e., from acetaldehyde or alkanes and alkenes by oxidation, by carbonylation of methanol, among others. Some of these other processes include the oxidizing of methylcyclohexane to produce acetic acid and formic acid, U.S. Pat. No. 3,247,249; vapor phase oxidation of ethyl alcohol in the presence of a solid palladium metal containing catalyst, U.S. Pat. No. 3,739,020; liquid phase oxidation of ethyl alcohol in the presence of at least one ketone such as methylethyl ketone and at least one aldehyde such as acetaldehyde and using air, cobalt acetate catalyst and acetic acid reaction medium, U.S. Pat. No. 3,914,296.

It is well-known that carboxylic acids such as acetic acid can be produced by several other liquid phase processes including the liquid phase oxidation of various organic compounds, such as ethanol to acetic acid. For example, in U.S. Pat. No. 2,425,878, a liquid phase oxidation process involves the direct reaction of a lower aliphatic alcohol, ethanol, with oxygen in a liquid phase reaction to prepare acetic acid wherein a rare earth metal catalyst is activated by an aldehyde. Large amounts of catalyst and activator are required.

In the past, high rates of conversion have been obtained in the utilization of ethanol to prepare acetic acid by use of an activator or promoter, as for example, when an aldehyde such as acetaldehyde is used as an activator, as in U.S. Pat. No. 2,578,306.

Although excellent yields of acetic acid are obtained, large amounts of promoter are required, from 1.6 to 9 moles acetaldehyde/mole ethanol oxidized (see U.S. Pat. No. 2,578,306), and from 0.41 to 1.26 moles, acetaldehyde plus methyl ethyl ketone/mole ethanol, oxidized (see U.S. Pat. No. 3,914,296). The problem with using such large amounts of acetaldehyde and methylethyl ketone to prepare acetic acid from ethanol is while these compounds oxidize to form acetic acid themselves, these compounds cost more than ethanol or acetic acid and are not commercially available in large enough amounts to make a large scale ethanol-to-acetic acid process practical. The instant invented process uses a cobalt, manganese, and bromine catalyst system and does not require additional promoters.

Oxidation of ethanol to acetic acid using a cobalt, manganese, bromide catalyst is taught in U.S. Pat. No. 3,247,249, "Preparation of Formic and Acetic Acids by Oxidizing Methylcyclohexane or Paraffin Wax in the Presence of Manganese Bromide." The yield of acetic acid and selectivity to acetic acid are far lower using the reaction conditions described in U.S. Pat. No. 3,247,249 than yields obtained by other processes, including yields obtained by processes using an activator or promoter. Yields of acetic acid given in the examples range from 12 to 19 mole % with formic acid being the major product in 61 to 64 mole % yield.

The bromine-polyvalent-metal catalysis system in acetic acid solvent has been in commercial use in many countries for the manufacture of terephthalic acid from p-xylene for many years. In the absence of acetic acid solvent, yield of a single phthalic acid (e.g., terephthalic acid) on a once through basis of the xylene, amounted to about 20 weight percent (12.8 mole), according to U.S. Pat. No. 2,833,816. Since terephthalic acid, for example, is the starting material for polyethylene terephthalic (PET) which is the principal polymer for polyester fibers, polyester films, and resins for bottles and like containers, the importance of acetic acid in the preparation of terephthalic acid, and in the preparation of other aromatic polycarboxylic acids, cannot be doubted.

In the oxidation of polyalkyl aromatics to polycarboxylic acids in the presence of acetic acid, as a solvent, some acetic acid is oxidized to carbon oxides and other oxidation by-products, which, coupled with physical losses, requires a constant addition as make-up to the oxidation process. Large quantities of acetic acid accordingly are required to supply the required amount of acetic acid necessary for production of, as an example, terephthalic acid on a commercial scale.

However, despite the availability of acetic acid from many sources, the singular importance of acetic acid as a solvent in production of polycarboxylic acids from alkyl aromatics, and the possibility of an interruption in the supply of acetic acid from conventional processes, mandated a search for a process to generate acetic acid in situ with the oxidation of polyalkyl aromatics to polycarboxylic aromatic acids.

It has been discovered that utilization of a cobalt-manganese-bromine-containing catalyst without added promoters in the preparation of terephthalic acid from p-xylene, isophthalic acid from m-xylene, and the preparation of trimellitic acid from pseudocumene makes possible the production of acetic acid from ethanol in high conversion, good selectivity and yield wherein the resulting acetic acid is the solvent of choice for oxidation of p-xylene to terephthalic acid, or oxidation of m-xylene to isophthalic acid, or oxidation of pseudocumene to trimellitic acid. In the process of this invention, formic acid is not produced as the major product, in contrast to the process of U.S. Pat. No. 3,247,249, wherein formic acid is the major product in 61 to 64 mole % yield and yields of acetic acid range from 12 to 19 mole %.

It is an object of the instant invention to provide a process for the production of acetic acid as a co-product in the oxidation of polyalkyl aromatics to polycarboxylic aromatic acids.

It is an object of the instant invention to provide a catalytic process for production of acetic acid as a co-product in the oxidation of polyalkyl aromatics to polycarboxylic acids wherein the catalyst comprises a variable valence oxidation catalyst in the presence of a bromine ion, preferably a cobalt-manganese catalyst in the presence of bromine ion.

It is an object of the instant invention to provide a catalytic process for production of acetic acid as a co-product in the oxidation of polyalkyl aromatics to polycarboxylic acids wherein the catalyst comprises cobalt-manganese-bromine, ethyl alcohol is oxidized to acetic acid, and production of formic acid, as a co-product from oxidation of ethyl alcohol, is minimized.

It is an object of the instant invention to provide a catalytic process for production of a $C_2$–$C_6$ aliphatic monocarboxylic acid as a co-product in the oxidation of polyalkyl aromatics to polycarboxylic acids and wherein the catalyst comprises cobalt-manganese-bromine, wherein a $C_2$–$C_6$ lower aliphatic alkanol is oxidized to a corresponding $C_2$–$C_6$ aliphatic monocarboxylic acid.

SUMMARY OF THE INVENTION

A process is disclosed by the co-production of acetic acid from ethyl alcohol in a reaction to prepare polycarboxylic aromatic acids from polyalkyl aromatics wherein the catalyst comprises cobalt-manganese-bromine and the solvent is acetic acid.

DETAILS OF THE INVENTION

The instant invented process for co-production of a suitable solvent can be used with any polyalkyl aromatic such as o-, m- and p-xylene, the trimethylbenzenes, and polyalkyl naphthalenes, wherein the respective aromatic polycarboxylic acid products are phthalic acid (OA), isophthalic acid (IA), terephthalic acid (TA), the tricarboxylic acids, and the naphthalene polycarboxylic acids. Suitably the alkyl groups of the polyalkyl aromatics contain from 1 to 6 carbon atoms and preferably are methyl groups. In a preferred embodiment of the method of this invention, p-xylene is oxidized to terephthalic acid and ethanol is oxidized to acetic acid.

It is essential that the process of the instant invention take place as a co-oxidation wherein a $C_2$–$C_6$ aliphatic alkanol is oxidized to a $C_2$–$C_6$ aliphatic monocarboxylic acid and a polyalkyl aromatic is oxidized to a polycarboxylic aromatic acid. In absence of the polyalkyl aromatic, for example, formic acid can be formed as a major product from ethanol. The presence of the polyalkyl aromatic suppresses formation of formic acid particularly in batch oxidation.

It is essential that the reaction solvent comprise the $C_2$–$C_6$ aliphatic monocarboxylic acid which is co-generated with the polycarboxylic aromatic acid. Generation of mixtures of aliphatic monocarboxylic acids induce the possibility of many undesirable by-products which necessitate extensive purification.

It is essential that the weight ratio of the polyalkyl aromatic to the total amount of solvent be at least 19:1 wherein the water component of the solvent be no more than 50 weight percent of total solvent.

Although suitable solvents for preparation of aromatic polycarboxylic acids include any aliphatic $C_2$–$C_6$ monocarboxylic acid such as acetic acid, propionic acid, n-butyric acid, isobutyric acid, n-valeric acid, trimethylacetic acid and caproic acid and water and mixtures thereof, preferably the solvent is a mixture of acetic acid and water, which more preferably contains from 1 to 20 weight percent of water, as introduced into the oxidation reactor. Since heat generated in the highly exothermic liquid phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After removal of the aromatic polycarboxylic acid product from the product stream, at least a portion of the mother liquor solvent in the resulting product stream is generally recycled to the reactor with any necessary make-up solvent. The weight ratio of the total amount of solvent in the reactor to the amount of the polyalkyl aromatic introduced into the reactor in the liquid phase oxidation of this invention is in the range of from about 19:1, preferably from about 6:1, to about 1:1, more preferably to about 3:1, solvent:polyalkyl aromatic. Make-up solvent can be from 0.1 to 10 wt. % of the total solvent in the reactor. Higher amounts up to 50 wt. % of solvent can be added in order to produce acetic acid to be used for another purpose.

Make-up solvent can either be acetic acid, as such, in the case wherein the solvent is an acetic acid-water mixture or in the process of this invention, ethanol can be added to the reactor to be oxidized in situ to acetic acid concurrently with the oxidation of polyalkyl aromatics to aromatic polycarboxylic acids. The instant invented process accordingly allows a choice of alternative make-up solvents which increases the utility of the overall oxidation process for production of aromatic polycarboxylic acids.

In like manner, in the event aliphatic $C_3$–$C_6$ monocarboxylic acids such as propionic acid, n-butyric acid, etc., are used as solvents, make-up solvent can either be propionic acid, n-butyric acid, etc., or propanol, or n-butanol, or isobutanol, etc., can be added to the reactor to be oxidized in situ to the required $C_3$–$C_6$ monocarboxylic acid concurrently with the oxidation of the polyalkyl aromatics.

The source of molecular oxygen employed in the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, when each alkyl substituent on the aromatic ring of the polyalkyl aromatic is a methyl group, a feed rate of the amount of from 1.5 to 2.8 moles per methyl group will provide such 0.5 to 8 volume percent of oxygen (measured on a solvent-free basis) in the gas-vapor mixture in the condenser.

The catalyst employed in the method of this invention comprises cobalt, manganese and bromine components, and can additionally comprise accelerators known in the art. The weight ratio of cobalt (calculated as elemental cobalt) in the cobalt component of the catalyst-to-polyalkyl aromatic in the liquid phase oxidation of the method of this invention is in the range of from about 0.2 to about 10 milligram atoms (mga) per gram mole of polyalkyl aromatic. The weight ratio of manganese to cobalt where manganese and cobalt are calculated as elemental manganese and cobalt, is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid phase oxidation of the method of this invention is in the range of from about 0.2 to about 1.5 mga per mga of total cobalt and manganese.

Each of the cobalt and manganese components can be provided in any of its known ionic or combined forms that provide soluble forms of cobalt, manganese and bromine in the solvent in the reactor. For example, when the solvent is an acetic acid medium, cobalt and/or manganese carbonate, acetate tetrahydrate, and/or bromide can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzyl-bromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine to total cobalt and manganese milligram atom ratio of 0.2:1.0 to 1.5:1.0. The bromide ion released from the organic bromides at the oxidation operating conditions can be readily determined by known analytical means. Tetrabromoethane, for example, at operating temperatures such about 340° F. (170° C.) to about 440° F. (225° C.) has been found to yield about 3 effective gram atoms of bromine per gram mole.

In operation, the minimum pressure at which the reactor is maintained is that pressure which will maintain a substantial liquid phase of the polyalkyl aromatic and at least 70 percent of the solvent. The polyalkyl-romatic and solvent not in the liquid phase because of vaporization is removed from the reactor as a vapor-gas mixture, condensed and then returned to the reactor. When the solvent is an acetic acid-water mixture, suitable reaction gauge pressure is in the range of from about 0 $kg/cm^2$ to about 35 $kg/cm^2$, and typically is in the range of from about 10 $kg/cm^2$ to about 30 $kg/cm^2$. The temperature range within the reactor is generally from about 250° F. (120° C.), preferably from about 300° F. (150° C.), to about 465° F. (240° C.), preferably to about 445° F. (230° C.).

In operation, the instant invented process can be used to generate all or an excess of make-up acetic acid solvent. The excess acetic acid can be recovered downstream for other applications. The amount of ethanol added to the process can meet with make-up requirements or to provide an excess of acetic acid, from 0.1 wt. % to 100 wt. %, percent of ethanol to hydrocarbon.

The instant invented process can be operated in either a batch, semi-continuous or continuous mode, depending upon the method most suited for oxidation of the polyalkyl aromatic. For example, trimellitic anhydride has been found to be suitably produced in a batch mode, wherein terephthalic acid is suitably produced in a semi-continuous or continuous mode.

In summary, the instant invention comprises a batch, semi-continuous or continuous liquid phase process for the co-preparation of an aliphatic monocarboxylic acid of from 2 to 6 carbon atoms and an aromatic polycarboxylic acid which comprises passing a feed in liquid phase comprising a lower aliphatic alkanol of 2 to 6 carbon atoms and a polyalkyl aromatic into a reaction zone containing a cobalt-manganese-bromine catalyst, reacting said alkanol and said polyalkyl aromatic with an oxygen-containing gas in a residence time of from about 10 minutes to about 240 minutes, preferably from about 30 minutes to about 120 minutes in the presence of said catalyst at a temperature of from about 250° F. to about 465° F., gauge pressure is within the range of from about 0 $kg/cm^2$ to about 35 kg/cm2, said reaction zone containing a solvent comprising water and an aliphatic monocarboxylic acid of 2 to 6 carbon atoms wherein the weight ratio of said solvent mixture to said polyalkyl aromatic is in the range of from 19:1 to about 1:1, wherein water content is no more than 50 weight percent of the solvent, and recovering reaction products comprising a monocarboxylic acid and an aromatic polycarboxylic acid. In more detail, the said lower alkanol is passed into said reaction zone and is reacted in situ with said oxygen-containing gas to an aliphatic monocarboxylic acid of 2 to 6 carbon atoms and said aliphatic monocarboxylic acid of 2 to 6 carbon atoms remains in said reaction zone as a component of said solvent. The said lower aliphatic alkanol is present in said feed in an amount within the range of from about 0.1 wt % to 100 wt % of said polyalkyl aromatic. The said lower aliphatic alkanol of 2 to 6 carbon atoms is selected from the group consisting of ethanol, n-propanol, n-butanol, isobutanol, amyl alcohol and n-hexyl alcohol. Preferably, said lower aliphatic alkanol is ethanol and said aliphatic monocarboxylic acid is acetic acid, and said solvent contains from about 1 to about 50 wt % water and from about 50 to 99 wt % acetic acid. Preferably, in a continuous or semi-continuous mode of operation, the polyalkyl aromatic is p-xylene and the lower aliphatic alkanol of 2 to 6 carbon atoms is ethanol. Preferably in a batch mode of operation, the polyalkyl aromatic is pseudocumene and the lower aliphatic alkanol of 2 to 6 carbons is ethanol.

The following examples illustrate the process of the invention but are not to be construed as limiting the scope of the invention.

EXAMPLE I

A 15-liter continuous stirred tank reactor having titanium-lined inside walls was used. The reactor was equipped with an overhead condenser for condensation of the solvent and p-xylene which vaporized in the reactor during the exothermic liquid phase oxidation and also for return of the condensed material to the reaction mixture in the reactor.

The oxidations were single stage, continuous, at 382° F. The co-oxidations employed the same temperature, catalyst loading, catalyst composition, percent oxygen in the vent, reactor solvent ratio, reactor solvent water concentration and residence time (hydrocarbon throughput).

The feed contained 24.5 wt. % p-xylene, 2.2 wt. % ethanol and 1.8 wt. % water. The balance was acetic acid. The catalyst comprised cobalt, manganese and bromine components which were in the form of soluble $Co(C_2H_3O_2)_2.4H_2O$, $Mn(C_2H_3O_2)_2.4H_2O$ and hydrobromic acid, respectively. The cobalt component, calculated as elemental cobalt, was present in the solvent in the reactor at a level of 370 parts per million by weight. The ratio of the number of gram atoms of the manganese component, calculated as elemental manganese, per gram atom of the cobalt component, calculated as elemental cobalt, was 2.6, and the ratio of the number of gram atoms of the bromine component, calculated as elemental bromine, per gram atom of the combined cobalt and manganese components, calculated as elemental cobalt and elemental manganese was 0.5. Oxygen concentration (measured on a solvent-free basis) in the gas-vapor mixture in the condenser was 3 vol. %.

The solvent was acetic acid and water, of which 13 wt. % was water. Reaction residence time was 66 minutes. Reaction conditions are summarized in Table I. Once through terephthalic acid yield was 93.9 mole %. Acetic acid yield from ethanol on a once through basis was 62 mole %, with recycle was 73 mole %.

TABLE I

| Reaction Conditions | Reaction Conditions Observed | Unit |
|---|---|---|
| Temperature | 382 | °F. |
| Pressure | 14(200) | kg/cm$^2$(psig) |
| Mn/Co | 2.6 | mole/mole |
| Br/Metals | 0.5 | mole/mole |
| Solvent Ratio | 3.0 | lb solvent/lb pX |
| Residence Time | 66 | minutes |
| Reactor Solvent Water | 13 | wt % in the solvent |
| Vent Oxygen | 3 | volume % in the dry vent gas |

EXAMPLE II

In the procedure of Example I, an oxidation run was performed with 115 wt. % of catalyst loading of Example I. Feed and other conditions were the same as in Example I except that ethanol was fed at a rate of 2.4 wt % of total feed. About 71 to 73 mole % of the ethanol as converted to acetic acid with the yield determined by difference. That is, 27 to 29 to mole % of the ethanol remained unreacted, or formed intermediates and by-products. Terephthalic acid production was 95.0 mole %. Ethanol oxidation products are detailed in Table II.

The unreacted ethanol and ethyl acetate can be recycled and given an additional opportunity to oxidize to convert the 1.1 mole % ethanol and a portion of the 7.2 mole % ethyl acetate remaining in the reactor to acetic acid. With recycle, yield of acetic acid is 79 mole %.

TABLE II

| Ethanol Oxidation Products | |
|---|---|
| Ethanol Oxidation Products | Ethanol Consumed (mole %) |
| By-Products | |
| Ethyl Acetate | 16.6 |
| Carbon Oxides | 7.4–9.1 |
| Unreacted Ethanol | 1.8 |
| Acetaldehyde | 0.9 |
| Other | 0.8 |
| Total Yield By-Products | 27.5 to 29.2 |

TABLE II-continued

| Ethanol Oxidation Products | |
|---|---|
| Ethanol Oxidation Products | Ethanol Consumed (mole %) |
| Acetic Acid Produced | |
| Yield By Difference | |
| Once Through | 70.8–72.5 |
| With Recycle | 79 |

Note:
Amount of ethanol consumed determined by calculation from analysis of products stream. Analysis was by gas chromatography.

EXAMPLE III

The following example illustrates that reduction of ethanol concentration does not appreciably reduce p-xylene oxidation. In the procedure of Example I, an oxidation was performed wherein the feed contained 15% of the ethanol loading used in Example II. Reactor feed ethanol concentration was 0.35 wt. %. Despite the lower ethanol loading, the pX oxidation yield was approximately that of Example II. Terephthalic acid yield was 94.5 mole %. The ethanol yield on a once through basis was 48 mole % and on recycle was 57 to 69 mole %. A summary of Examples I, II and III is in Table III. Note that yield of terephthalic acid from p-xylene is maintained.

TABLE III

| Acetic Acid Yield and Catalyst Loading | | | |
|---|---|---|---|
| | Example | | |
| | I | II | III |
| Ethanol Conc. wt % Total Feed | 2.2 | 2.4 | 0.35 |
| Catalyst Loading | 100% | 115% | 100% |
| Acetic Acid Yield Mole % (Recycle) | 73 | 79 | 57–69 |
| Terephthalic Acid Yield Mole % | 93.9 | 95.0 | 94.5 |

EXAMPLE IV

The following example illustrates that the instant invented process can be used for the batch oxidation of pseudocumeme to trimellitic acid. Feed composition, including catalyst, was 225 g pseudocumeme, 420 g solvent, 1.63 g cobalt acetate hydrate, $Co(C_2H_3O_2)_2.4H_2O$, manganese acetate hydrate, $Mn(C_2H_3O_2)_2.4H_2O$, 0.34 g hydrobromic acid (HBr 48%), 0.05 g zirconium acetate solution (17 wt. % zirconium). In addition, a catalyst solution was added to the reaction continuously during the reaction which comprised 1.33 g hydrobromic acid (HBr 48%), 0.11 g manganese acetate hydrate, $Mn(C_2H_3O_2)_2.4H_2O$, 0.07 g zirconium acetate solution (17 wt. % zirconium). The base case used acetic acid as the solvent without any ethanol. Ethanol was substituted thereupon for acetic acid in the solvent. The ethanol was added at levels of 20 to 50% of total solvent (the balance being acetic acid and water). When the ethanol was in concentrations higher than 20%, the oxidation slowed down and the selectivity suffered. However, at 20% substitution the oxidation behaved much like a base case run with no ethanol. Table IV contains this comparison and shows a slight reduction in trimellitic anhydride (TMLA) yield due to small increases in the low boiling impurities such as isophthalic acid (IA), terephthalic acid (TA), and orthophthalic acid (OA).

Analysis of the reactor effluent showed little residual ethanol which indicates that ethanol was consumed and was converted to acetic acid. Analysis was by gas chromatography.

TABLE IV

Oxidation Products-Pseudocumene and Ethanol Batch Oxidation

| Ethanol wt % of Solvent | 0 | 20 | 50 |
|---|---|---|---|
| *Oxidation Products of Pseudocumene* | | | |
| Solids Recovered from Oxidation | | | |
| TMLA, wt % | 92.5 | 88.9 | 60.6 |
| OA, IA, TA, wt % | 1.75 | 2.05 | 2.45 |
| Methyl Diacids, wt % | 0.41 | 0.66 | 12.71 |
| High Boilers, wt % | 1.98 | 1.66 | 3.83 |
| $CO + CO_2$, mole % of Pseudocumene Charged | 5.0 | 5.1 | 5.0 |
| *Oxidation Products of Ethanol-Mole % of Ethanol Consumed* | | | |
| By-Products | | | |
| Ethyl Acetate | 0.0 | 8.7 | 7.2 |
| Carbon Oxides | 0.0 | 0.4 | 0.1 |
| Unreacted Ethanol | 0.0 | 1.1 | 1.3 |
| Acetaldehyde | 0.0 | 0.2 | 0.3 |
| Formic Acid | 0.0 | 1.53 | 15.5 |
| Total Yield By-Products | 0.0 | 15.3 | 24.4 |
| Acetic Acid Produced | | | |
| Yield by Difference | 0.0 | 74.3 | 75.6 |

The above data indicate that ethanol up to about 50 wt % can be substituted for an acetic acid solution in a batch oxidation of pseudocumene without major loss of ethanol to formic acid.

What is claimed is:

1. A liquid phase process for the co-preparation of an aliphatic monocarboxylic acid of from 2 to 6 carbon atoms and an aromatic polycarboxylic acid which comprises reacting in liquid phase a lower aliphatic alkanol of 2 to 6 carbon atoms and a polyalkyl aromatic in a reaction zone containing a cobalt-manganese-bromine catalyst, wherein weight ratio of said cobalt, calculated as elemental cobalt, is in the range of from about 0.2 to about 10 milligram atoms per gram mole of said polyalkyl aromatic, weight ratio of said manganese, calculated as elemental manganese, is in the range of from about 0.2 to about 10 milligram atoms per milligram atom of cobalt and weight ratio of said bromine, calculated as elemental bromine, is in the range of from about 0.2 to about 1.5 milligram atoms of total cobalt and manganese with an oxygen-containing gas in a residence time of from about 10 minutes to about 240 minutes, in the presence of said catalyst at a temperature of from about 250° F. to about 465° F., gauge pressure within the range of from about 0 $kg/cm^2$ to about 35 $kg/cm^2$, said reaction zone containing a solvent comprising water and an aliphatic monocarboxylic acid of 2 to 6 carbon atoms wherein the weight ratio of said solvent mixture to said polyalkyl aromatic is in the range of from 19:1 to about 1:1, and recovering reaction products comprising a monocarboxylic acid of from 2 to 6 carbon atoms and an aromatic polycarboxylic acid.

2. The process of claim 1 wherein said lower alkanol of from 2 to 6 carbon atoms is passed into said reaction zone and is reacted in situ with said oxygen-containing gas to an aliphatic monocarboxylic acid of from 2 to 6 carbon atoms and said aliphatic monocarboxylic acid remains in said reaction zone as a component of said solvent.

3. The process of claim 1 wherein said lower aliphatic alkanol is present in said feed in an amount within the range of from about 0.1 wt % to 100 wt % of said polyalkyl aromatic.

4. The process of claim 1 wherein said lower aliphatic alkanol of 2 to 6 carbon atoms is selected from the group consisting of ethanol, n-propanol, n-butanol, iso-butanol, amyl alcohol and n-hexyl alcohol.

5. The process of claim 1 wherein said lower alkanol is ethanol and said aliphatic monocarboxylic acid is acetic acid.

6. The process of claim 1 wherein said solvent contains from about 1 to about 50 wt % water and from about 50 to 99 wt % acetic acid.

7. The process of claim 1 wherein said residence time is from about 30 minutes to about 120 minutes.

8. The process of claim 1 wherein said oxygen-containing gas is air.

9. The process of claim 1 wherein weight ratio of said solvent mixture to said polyalkyl aromatic is in the range of from about 6:1 to about 1:1.

10. The process of claim 1 wherein weight ratio of said solvent mixture to said polyalkyl aromatic is 3:1.

11. The process of claim 1 wherein said polyalkyl aromatic is paraxylene, said lower aliphatic alkanol is ethanol and said process is in semi-continuous or continuous mode.

12. The process of claim 1 wherein said polyalkyl aromatic is pseudocumene, said lower aliphatic alkanol is ethanol and said process is in batch mode.

* * * * *

UNITED STATES PATENT OFFICE
CERTIFICATE OF CORRECTION

Patent No. 4,906,772            Dated   March 6, 1990

Inventor(s)   Calvin T. Chew, Rosemary F. McMahon, Kristi A. Fjare &
              Wayne P. Schammel It is certified that error appears in the above-identified patent and that said Letters Patent is hereby corrected as shown below:

| Col. | Line |  |
|------|------|--|
| 7 | 48 | "as" should read --was-- |
| 8 | 20-21 | "concentration was" should read --concentration was 0.35 wt.%-- |

Signed and Sealed this

Second Day of July, 1991

Attest:

HARRY F. MANBECK, JR.

Attesting Officer

Commissioner of Patents and Trademarks